(12) United States Patent
Higuma et al.

(10) Patent No.: US 6,547,722 B1
(45) Date of Patent: Apr. 15, 2003

(54) ENDOSCOPE HAVING RESISTANCE TO HIGH-TEMPERATURE AND HIGH-PRESSURE STEAM

(75) Inventors: Masakazu Higuma, Hachioji (JP); Yasuyuki Futatsugi, Hachioji (JP); Susumu Aono, Hachioji (JP)

(73) Assignee: Olympus Optical Co., Ltd. (JP)

( * ) Notice: Subject to any disclaimer, the term of this patent is extended or adjusted under 35 U.S.C. 154(b) by 63 days.

(21) Appl. No.: 09/613,370

(22) Filed: Jul. 10, 2000

(30) Foreign Application Priority Data

| Jul. 13, 1999 | (JP) | ............................................ | 11-199289 |
| Aug. 5, 1999 | (JP) | ............................................ | 11-222856 |
| Aug. 6, 1999 | (JP) | ............................................ | 11-224524 |
| Jun. 8, 2000 | (JP) | ............................................ | 2000-172344 |

(51) Int. Cl.[7] .................................................. A61B 1/04
(52) U.S. Cl. ..................................................... 600/133
(58) Field of Search ............................... 600/133, 112, 600/176, 122

(56) References Cited

U.S. PATENT DOCUMENTS

| 4,669,818 A | * | 6/1987 | Myer .......................... 385/139 |
| 4,779,613 A | | 10/1988 | Hashiguchi et al. |
| 4,805,598 A | * | 2/1989 | Ueda .......................... 359/665 |
| 5,536,244 A | * | 7/1996 | Muller et al. ............. 228/124.1 |
| 5,836,867 A | * | 11/1998 | Speier et al. .......... 403/DIG. 1 |
| 5,944,656 A | * | 8/1999 | Pollack et al. .............. 600/176 |
| 5,980,450 A | * | 11/1999 | Thompson ................... 600/112 |
| 6,030,339 A | * | 2/2000 | Tatsuno et al. ............. 600/112 |
| 6,033,360 A | * | 3/2000 | Sano et al. .................. 600/133 |
| 6,080,101 A | * | 6/2000 | Tatsuno et al. ............... 348/65 |
| 6,146,326 A | * | 11/2000 | Pollack et al. .............. 600/133 |
| 6,292,221 B1 | * | 9/2001 | Lichtman .................... 348/345 |
| 6,346,073 B1 | * | 2/2002 | Thompson ................... 600/112 |

FOREIGN PATENT DOCUMENTS

| DE | 19644729 | 1/1998 |
| JP | 10-234649 | 9/1998 |
| WO | 98/04948 | 2/1998 |

* cited by examiner

Primary Examiner—Linda C. M. Dvorak
Assistant Examiner—Kenneth G Schopfer
(74) Attorney, Agent, or Firm—Ostrolenk, Faber, Gerb & Soffen, LLP

(57) ABSTRACT

An endoscope having resistance to high-temperature and high-pressure steam including an optical unit having at least one optical member; and optical unit supporting frame for supporting the optical unit so that its position can be adjusted in the direction of the optical axis; and a hermetic optical covering member joined to the optical unit supporting frame and having an optical window for covering at least an end portion of the optical unit when it is joined.

28 Claims, 15 Drawing Sheets

ENDOSCOPE HAVING RESISTANCE TO HIGH-TEMPERATURE AND HIGH-PRESSURE STEAM

This application claims the benefit of Japanese Application Nos. Hei. 11-199289, filed in Japan, on Jul. 13, 1999, Hei. 11-222856, filed in Japan, on Aug. 5, 1999, Hei. 11-224524, filed in Japan, on Aug. 6, 1999, 2000-172344, filed in Japan, on Jun. 8, 2000, the contents of which are incorporated herein.

BACKGROUND OF THE INVENTION

1. Field of the Invention

The present invention relates to an endoscope which is characterized in the structure of contents disposed in a space within the endoscope and which accommodates to autoclave sterilization.

2. Related Art Statement

An endoscope which allows an operator to observe deep inside of a body cavity by inserting an insert section thereof and to carry out remedial operations by using operation tools as necessary has come to be widely used lately.

In case of a medical endoscope, it is essential to sterilize and disinfect the endoscope following use to prevent infectious diseases and the like. Hitherto, surgeons have achieved this disinfecting and sterilization process with sterilization gas, such as ethylene oxide gas (EOG) and on disinfectant solutions.

However, as it has been known widely, it has been cumbersome to carry out disinfecting and sterilization by sterilization gas. There has been also a problem that the tool cannot be used right away after such sterilization because it takes time for aeration to remove the gas adhered to the tool after sterilization. Still more, it has been a problem that its running cost is high.

Use of a disinfectant solution has had drawbacks in that it is cumbersome to control the solution and that it takes much cost for disposal of such solution.

Autoclave sterilization, or high-pressure steam sterilization, which requires no cumbersome works and allows the tools to be used right away after sterilization and has a running cost that is low is now becoming the mainstream of endoscope disinfecting and sterilization processes.

The typical conditions of the autoclave sterilization are described in the US Standard ANSI/AAMI ST37-1992 authorized by the American Standards Association and published by the Medical Equipment Development Association and published by the Medical Equipment Development Association. According to the conditions, the sterilization step had to be carried out at 132° C. for four minutes in a pre-vacuum type or at 132° C. for ten minutes in a gravity type.

The autoclave sterilization is actually carried out by infiltrating steam in a range of about 120° C. to 140° C. about a subject to be sterilized under high pressure of about 0.2 Mpa.

However, the high-temperature and high-pressure steam of autoclave sterilization has the ability of penetrating through polymer materials, such as rubber and plastics and adhesives, which are used for composing the endoscope. Accordingly, when the conventional endoscope, which is constructed to be water-tight endoscope with O-ring and adhesives, is sterilized by autoclave steam infiltrates through the water-tight endoscope.

When the steam infiltrates the endoscope by autoclave sterilization, the steam penetrates through the adhesives of the lens system and infiltrates the lens system. Therefore, there is a possibility that water drops remain on the lens surface or the lens and the adhesive for joining the lenses deteriorates, thus blocking the field of view.

Epoxy resin, which is adhesive, generally used for a long time, deteriorates when exposed to high-temperature steam. Therefore, it is possible that the steam is liable to infiltrate the lens systems as the adhesive peels off.

It also is possible that the adhesive peels off due to stress which occurs between parts due to differences of coefficients of thermal expansion of the materials composing the respective parts, thus the steam infiltrates the lens system because the temperature of autoclave sterilization is high.

A circuit board and electronic parts mounted on the circuit board, a joint part of the circuit board and lead wires and a joint part of the lead wires and connectors composing an image pickup device, for example, stored in he endoscope are coated and protected by epoxy adhesive or silicon adhesives. However, because the epoxy and silicon adhesives have high hygroscopic properties, there is a possibility that the circuit board and the electronic parts mounted on the circuit board, the joint part of the circuit board and the lead wires and the joint part of the lead wires and the connectors corrode by the high-temperature and high-pressure steam when the steam which has infiltrated the endoscope reaches those parts.

In view of these circumstance, hermetically closing the inside of the lens system by means of soldering has been used instead of jointing by the adhesives.

For instance, Laid-Open Japanese Patent Application No. Hei. 10-234649 has disclosed a hard scope which prevents cloudiness and deterioration of the lenses and deterioration of the adhesives by forming a hermetic package by hermetically assembling a cover glass at the front end of an inner cylindrical tube and by hermetically assembling a hermetic connector which can electrically connect the inside and the outside, while maintaining airtightness, to a rear end of the inner cylindrical tube and by inserting and assembling an objective lens system within the hermetic package. According to this arrangement, the objective lens group is fixed to a frame which holds the objective lens group in focus with respect to a solid image pickup device. The whole objective optical system composed of the focused objective lens group, the objective lens group holding frame and the solid image pickup device is inserted to the inner cylinder. It is noted that airtightness means tightness to a degree sustainable to the high-temperature and high-pressure steam of autoclave sterilization in the present application.

However, the hard scope in Laid-Open Japanese Patent Application No. Hei. 10-234649 has had a drawback in that the outside shape of the insert section is large because the hermetic package is provided within the insert section.

That is, although the arrangement described above may be adopted for the hard scope, which permits the hermetic package of the objective optical system to be long, it is hardly adoptable for a scope having a bend in which the hermetic package of the objective optical system must be stored at the front end beyond the bend section. When this arrangement is adopted for an endoscope having a bend, it causes a trouble in that the hard lengthy part at the front end beyond the bend section becomes long, thus increasing a burden on patients.

It is noted that steam infiltrating an endoscope during autoclave sterilization adheres to an angle wire in the endoscope in which wires formed by stranded wires by bundling metallic element wires, such as conventional stainless wires, is used as the angle wire for controlling the bend section of the endoscope. This creates a possibility that the angle wire rusts as the steam remains in the gap between the element wires.

The angle wire has been coated variously to increase slippage thereof for a long time. However, the coating has not been carried out steadily in the gap between the element wires and in the part not contacting with other parts, so that it could not prevent rust across the whole wire.

Further, de-flick coat, which is coating containing molybdenum disulfide, which has been used as a coating material in general for a long time, is not only unable to coat the gap between the element wires, but also is deteriorated and peeled off by the high-temperature and high-pressure steam of autoclave sterilization. Therefore, the de-flick coat did not function as a rust preventive coating at all.

OBJECTS AND SUMMARY OF THE INVENTION

Accordingly, it is an object of the invention to provide an endoscope which is susceptible to autoclave sterilization and which allows an optical unit disposing section to be formed small and to be disposed at the front-end portion of an endoscope having a bend.

Another object of the invention is to provide an endoscope which is susceptible to autoclave sterilization and which allows an optical unit to be assembled favorably.

A further object of the invention is to provide an endoscope which is susceptible to autoclave sterilization and which has an optical unit constructed at low cost.

Yet another object of the invention is to provide an endoscope which experiences no failure of the bend due to problems with an angle wire, even if autoclave sterilization is carried out.

Briefly, the inventive endoscope which can endure high-temperature and high-pressure steam comprises an optical unit having at least one optical member; an optical unit supporting frame for supporting the optical unit so that the position thereof can be adjusted in the direction of an optical axis; and a hermetic optical covering member which is joined to the optical unit supporting frame and has an optical window covering at least the end portion of the optical unit when it is joined.

BRIEF DESCRIPTION OF THE DRAWINGS

FIGS. 1 through 13 are drawings explaining a first embodiment of the invention, wherein:

FIG. 1 is a side perspective view of the endoscope of the present invention;

FIG. 2 is a selection view of a CCU connector;

FIG. 3 is a section view of a front-end section of an insert section;

FIG. 4 is a schematic view of the structure of an angle wire;

FIG. 5 is a section view of an image pickup unit;

FIG. 8 is a section view of a solid image pickup device fixed on the back of a rear-end hermetic optical covering member;

FIG. 9 is a section view of an insulating frame secured at the front face of the rear-end hermetic optical covering member;

FIG. 10 is a partially cutaway section view of the insulating frame;

FIG. 11 is a section view of the assembly of the front-end hermetic optical cover member;

FIG. 12 is a section view of a hermetic objective lens unit;

FIG. 13 is a schematic view of another structural example of the angle wire;

FIGS. 14 and 15 are drawings explaining a second embodiment of the invention, wherein: FIG. 14 is a section view of an image pickup unit having a hermetic objective lens unit of another construction; and FIG. 15 is a section view of a front-end hermetic optical cover member;

FIGS. 16 through 19 are drawings explaining a third embodiment of the invention, wherein FIG. 16 is a section view of the image pickup unit; FIG. 17 is a section view of the image pickup unit without an optical window; FIG. 18 is a section view of the front-end hermetic optical cover member; FIG. 19 is a section view of the image pickup unit where an optical system in which an objective lens group cannot form an image perfectly;

DETAILED DESCRIPTION OF EMBODIMENTS OF THE INVENTION

Embodiments of the invention will be explained below with reference to the drawings.

A first embodiment of the invention will be explained below with reference to FIGS. 1 through 13.

Figure 1:
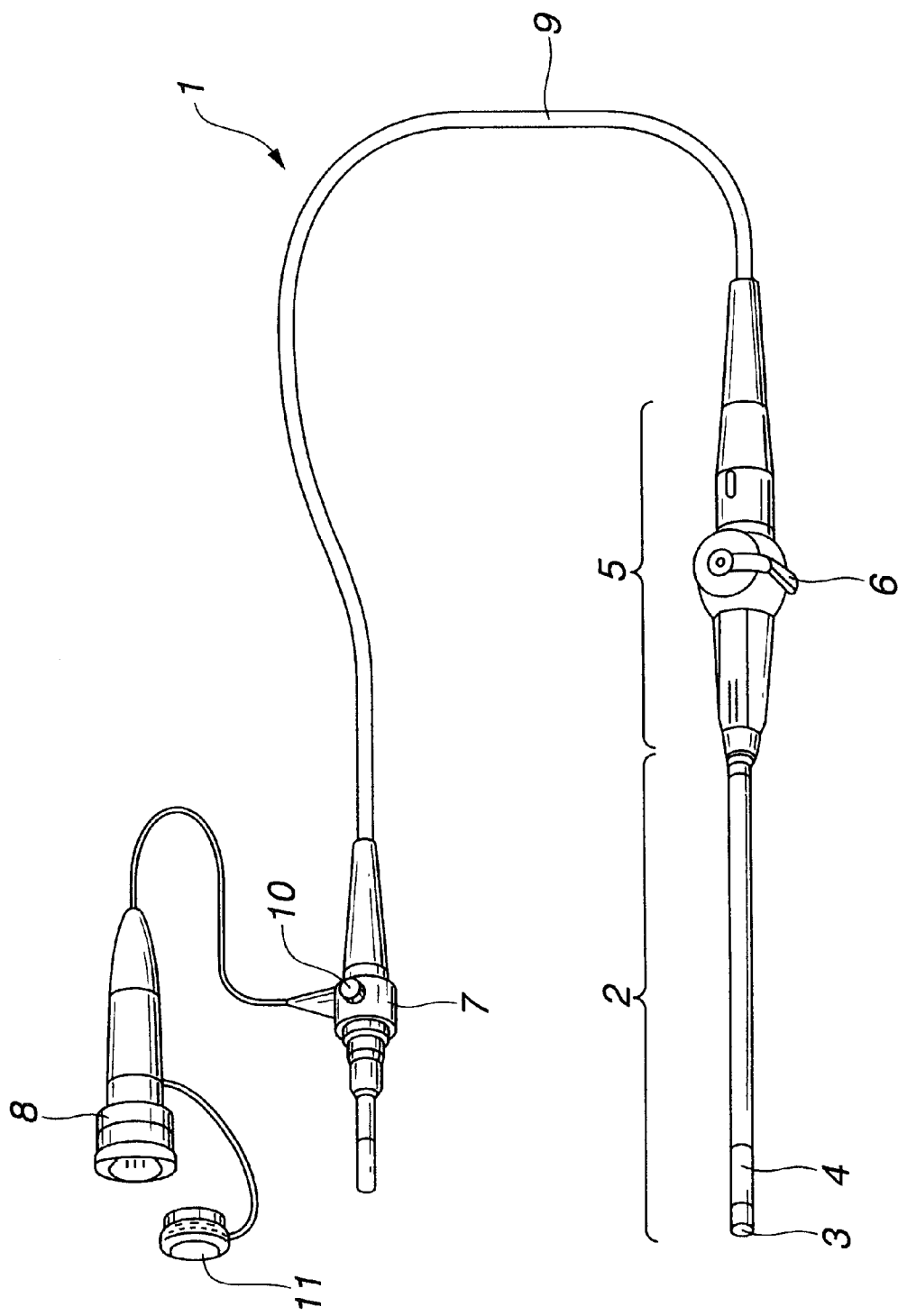

As shown in FIG. 1, and endoscope has a soft insert section 2, which is to be inserted into a body, at the front-end part of the main body of the endoscope 1. The insert section 2 comprises a front-end section 3 and a bend section 4. There is also provided a control section 5 at the basal end portion of the insert section 2. The control section 5 comprises an angle lever 6 for remotely controlling the bend section 4.

The endoscope 1 also comprises a connector 7, for connecting the endoscope 1 to a light source unit (not shown), and a CCU connector 8, for connecting the endoscope 1 to a video system center. The connector 7, the CCU connector 8 and the control section 5 are connected via a flexible cord 9.

The connector 7 is provided with a switch valve 10 which communicates with the internal space of the endoscope 1 and can be opened and closed by an adapter (not shown). The switch valve 10 has a check valve structure which communicates with the internal space when pressure of the internal space of the endoscope 1 becomes higher than the outside pressure by predetermined pressure. This structure of the switch valve 10 prevents the soft parts within the partition wall of the endoscope, such as bend rubber, of the bend section 4 of the endoscope, from breaking even if the inside of the chamber is evacuated in the pre-processing step of autoclave sterilization. The switch valve 10 may be constructed such that a check valve adapter (not shown) is assembled beside the check valve structure.

Figure 2:
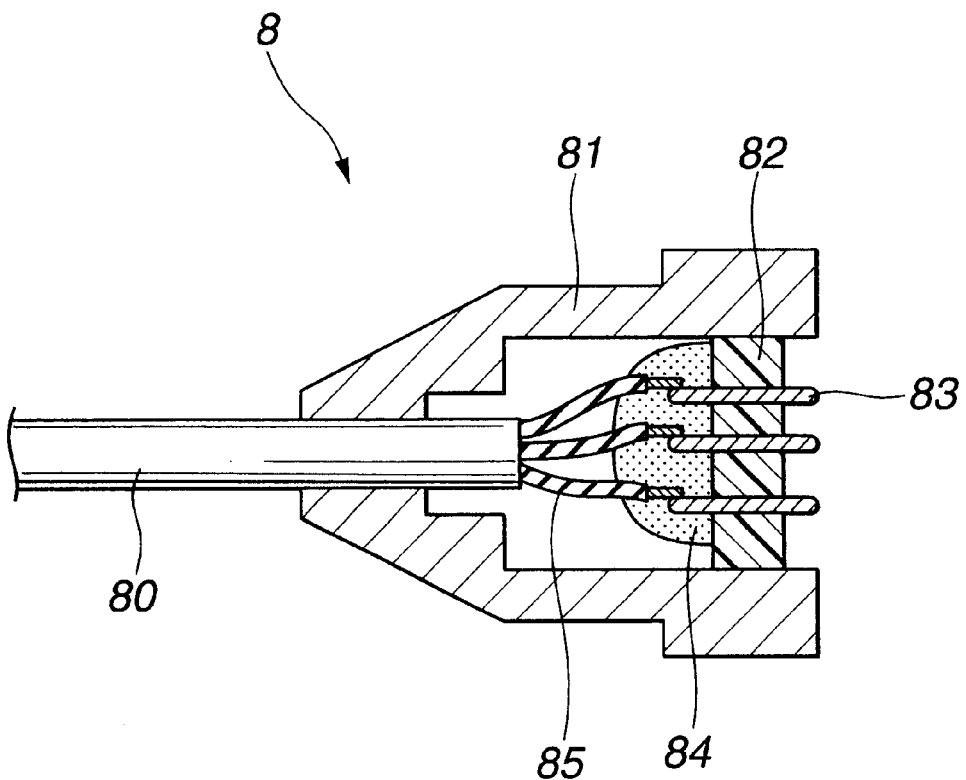

As shown in FIG. 2, the CCU connector 8 comprises a cylindrical frame body 81, having a through hole into which a front end of the CCU cable 80 is inserted, a lid 82, which closes an opening of the frame body 81, a plurality of connector pins 83, which are secured to through holes created through the lid 82 and which electrically connect the interior with exterior electrical components, lead wires 85, which are electrically connected with the connector pins 83 by solder or the like within the frame body 81, and a sealant 84, for sealing the part where the connector pins 83 are connected with the lead wires 85. A waterproof cap 11, which makes the electrical connector section comprising the connector pins 83 watertight, is assembled to the CCU connector 8. The main body of the endoscope 1 has a watertight structure by which not water infiltrates into the endoscope 1.

The sealant 84 is made of insulating fluoro-rubber having low steam permeability. The main component of the fluoro-rubber is fluoro-silicon resin, fluoro-polyether or per-fluoro-polyether polymer, for instance.

Figure 3:
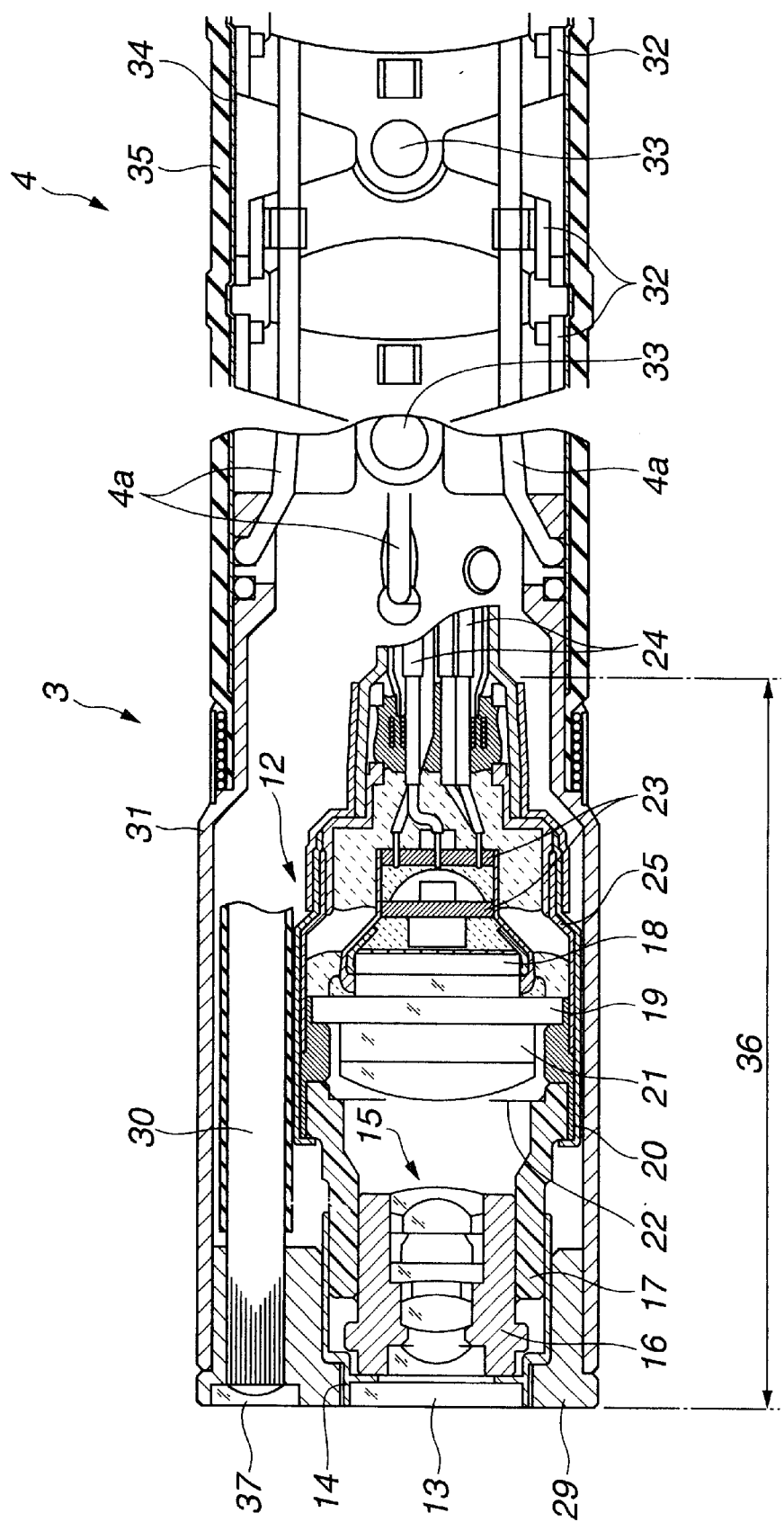
Figure 5:
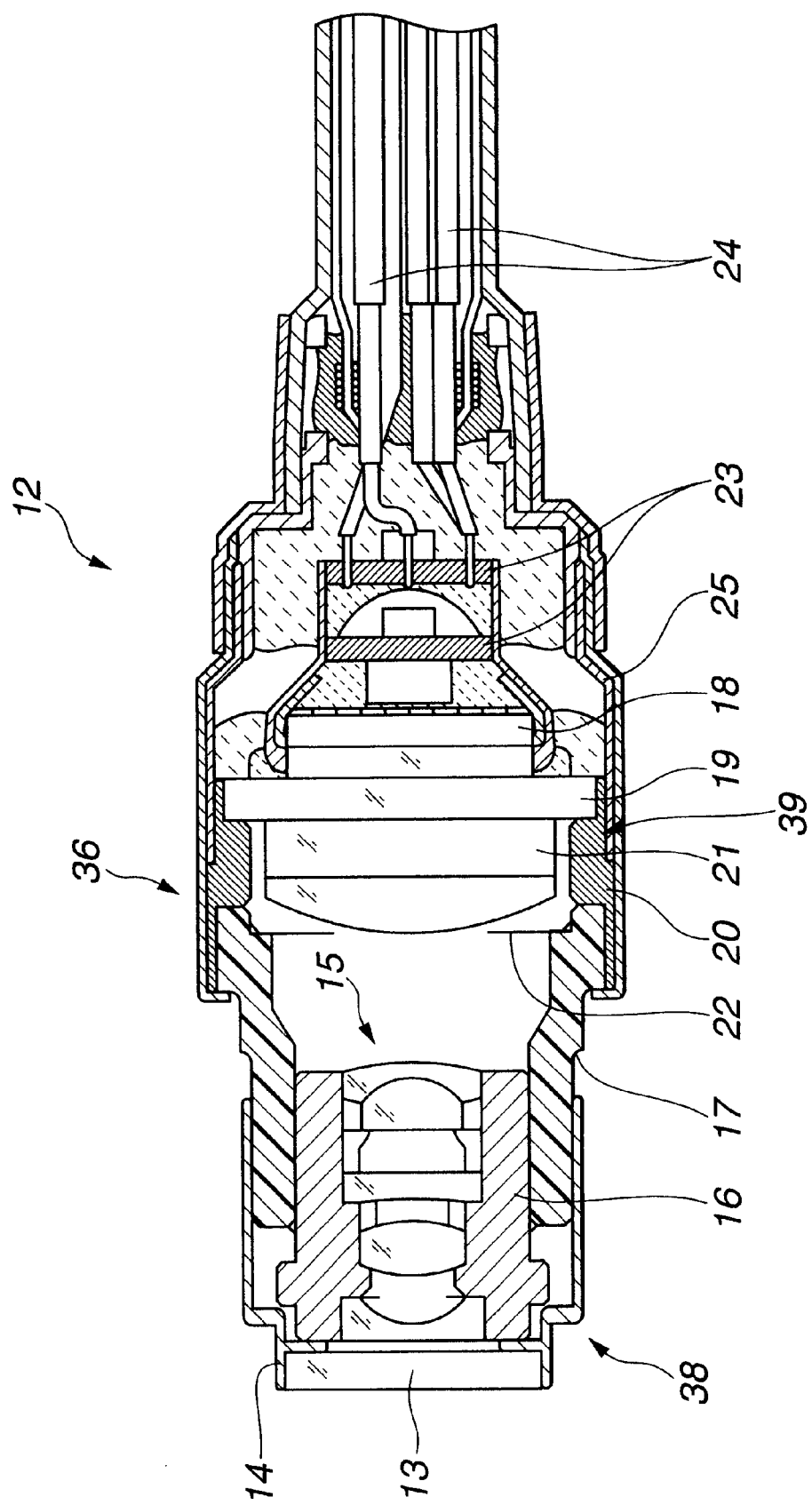

As shown in FIG. 3, an image pickup unit 12, a light guide fiber 30 and other parts are assembled in a front-end component 29, which forms the front-end section 3 of the insert section 2. An illumination lens 37 is disposed at the front-end of the light guide fiber 30.

A front-end covering member 31 is assembled around the front-end component 29. A plurality of bend pieces 32, which form the bend section 4, are assembled behind the front-end covering member 31. These bend pieces 32 are turnably linked to each other by a rivet 33 and are coated by a metallic net tube 34 and bend rubber 35. The angle wires 4a are attached to the basal end portion of the front-end covering member 31.

Figure 4:
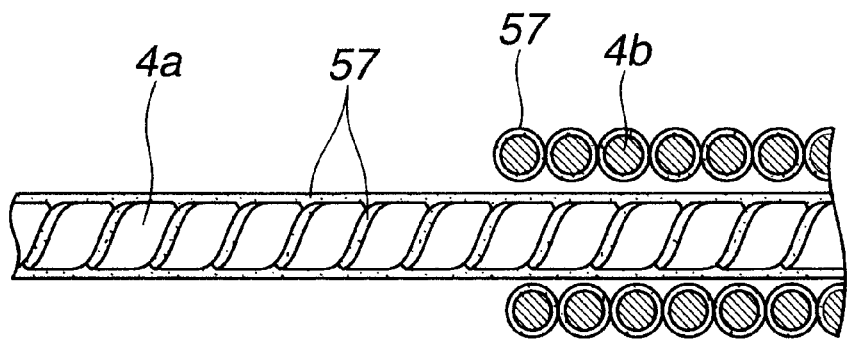

The angle wire 4a is a stainless wire obtained by stranding stainless element wires, for instance, as shown in FIG. 4. Rust preventive material 57 having resistance to high-temperature and high-pressure steam is filled in the gap between the respective element wires of the angle wire 4a and is coated around the outer surface of the wire.

Then, while a stainless angle coil 4b is used as a guide member of the angle wire 4a disposed within the insert section 2 in the present embodiment, the rust preventive material 57 is coated also around the surface of the angle coil 4b. The element wire is not limited to the stainless wire, metallic wires having high corrosion resistance, such as tungsten wire and titanium alloy wire, may be adopted. When the tungsten wire is used, it is more effect to use an electrolytic tungsten wire because it has higher corrosion resistance.

It becomes possible to prevent the element wire from being exposed to steam during the autoclave sterilization by filling the rust preventive material 57 in the gap between the respective element wires of the angle wire 4a and by coating the surface of the angle wire 4a.

It also becomes possible to prevent the element wire from being exposed to steam by coating the rust preventive material 57 on the surface of each element wire of the angle wire 4a and by creating the angle wire 4a by bundling the element wires coated by the rust preventive material, because the wire element material is not exposed to the gap between the element wires as a result.

The material having resistance to high-temperature and high-pressure steam, such as fluoro-resin material, Flexible diamond-like hard carbon material which is amorphous carbon hard material mainly composed of carbon and hydrogen, silica member converted from silazane, fluoro-resin paint containing graphite, fluoro-rubber paint, boron nitride containing material, PTFE nickel material and the like, may be used as the rust preventive material 57. The rust preventive material 57 may be used also as a rust preventive coating material having resistance to high-temperature and high-pressure steam. It is also possible to implement rust preventive coating by means of plating or the like as rust preventive coating using a rust preventive material such as metal.

A hard part 36 of the image pickup unit 12 is disposed at the front-end side from the first rivet 33 from the front-end side, i.e., within the front-end hard lengthy part, as shown in FIG. 3.

A cover glass 13, using sapphire, which is an optical window exposed to the outer surface of the insert section 2, is provided at the front end of the image pickup unit 12 and is hermetically joined to a metallic front-end cover frame 14.

The front-end cover frame 14 and the cover glass 13 form a front-end hermetic optical cover member 38. An optical unit, in which objective lens group 15 is assembled to a lens from 16, is disposed at the rear side of the cover glass 13. Nickel is electrically plated at the lower layer and gold is plated at the outermost layer of an inner peripheral plane of the front-end portion of the front-end cover frame 14.

The lens frame 16 is secured to a insulating frame 17, which is an optical unit supporting frame using an insulating materials, such as ceramics, and which holds the lens frame 16 by positioning in the direction of optical axis. Aluminum nitride, cyaron, black alumna or the like are used as the ceramic of the insulating frame 17. A stop 22 is secured to the insulating frame 17.

A solid image pickup device 18, which is an image pickup means, is positioned by a reticle or the like to a sapphire cover glass 19 and is secured thereto. A lens group 21 is positioned and secured to the other plane of the cover glass 19. The cover glass 19 is fitted and hermetically joined to a metallic frame 20.

The cover glass 19 and the frame 20 form a rear-end hermetic optical cover member 39. The other end of the frame 20 is received and hermetically joined to the outer periphery of the insulating frame 17. Nickel is electrically plated at the lower layer and gold is plated at the outermost layer of an inner peripheral plane of the front-end portion of the frame 20, similar to the inner peripheral plane of the front-end cover frame 14.

The solid image pickup device 18 is electrically connected to a cable 24 via a substrate 23 by soldering or the like. Electronic parts, such as ICs and capacitors, are packaged on the substrate 23 and are sealed by insulating adhesives or the like which transmit less steam and absorb less moisture.

A shield frame 25 is adhered or joined by means of welding with the frame 20 to the outside of the solid image pickup device 18. Fluoro-rubber sealant or oining agent having a low steam permeability is filled between the shield frame 25 and the solid image pickup device 18.

The procedure for assembling the endoscope will be explained with reference to FIGS. 6A through 12.

Figure 6A:
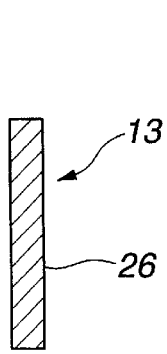
FIG. 6A is a schematic view of a single cover glass disposed at a front-end cover frame.
Figure 6B:
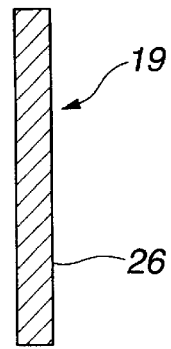
FIG. 6B is a schematic view of the single cover glass disposed at the frame.

The cover glasses 13 and 19 are made of sapphire and have a surface treatment of metal coating on the outer peripheral plane 26 thereof, as shown in FIGS. 6A and 6B.

The cover glasses 13 and 19 are not limited to being sapphire, any glasses having high heat resistance and high steam resistance may be used. The metal coating described above is composed of a chrome layer, provided at the lowest layer as a metallized layer, a nickel layer provided as a second layer, i.e., as an intermediate layer, and metal forming the top layer. Each layer is formed by evaporation or sputtering in vacuum or by plating.

Figure 7A:
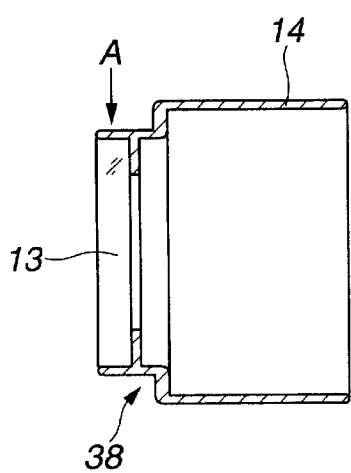
FIG. 7A is a section view of a front-end hermetic optical cover member.

The cover glass 13 is seated in a predetermined position on the front-end cover frame 14, as shown in FIG. 7A. Then, laser is irradiated onto the outer peripheral plane of the front-end cover frame 14, where the cover glass 13 is fitted, from the direction A. Then, gold at the outer peripheral plane of the cover glass 13 and gold provided at the outermost layer of the inner peripheral plane of the front-end cover frame 14 melt, respectively, due to the laser. The front-end hermetic optical cover member 38 is assembled by irradiating the laser onto the whole periphery of the front-end cover frame 14 and by cooling and coupling them thereafter.

It is preferable to use YAG laser, which may be controlled finely at low output. When a pulse wave laser is irradiated, air-tightness may be assured reliably by superimposing the neighboring pulses by more than 80%.

Figure 7B:
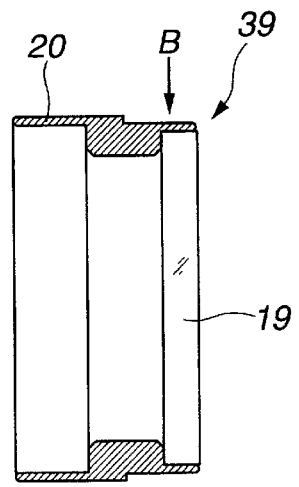
FIG. 7B is a section of a rear-end hermetic optical cover member.

Then, the rear-end hermetic optical cover member 39 is assembled in the same manner by seating the cover glass 19 in a predetermined position of the frame 20 as shown in FIG. 7B, and by hermetically joining the frame 20 with the cover glass 19 at the position B.

Figure 8:
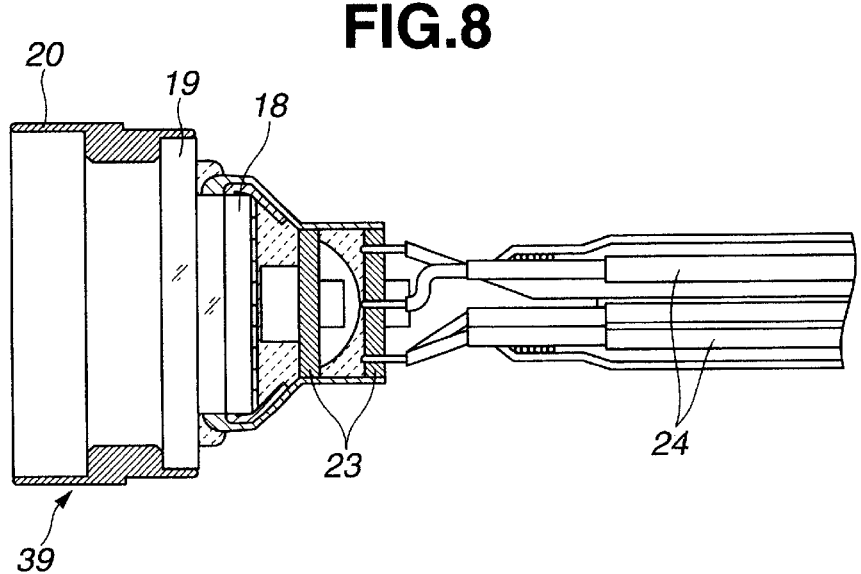

Next, the solid image pickup device 18, in which the substrate 23 and the cables 24 are assembled, is positioned on the back of the cover glass 19, as shown in FIG. 8, and adhered so that no air layer is created by translucent adhesive.

Figure 9:
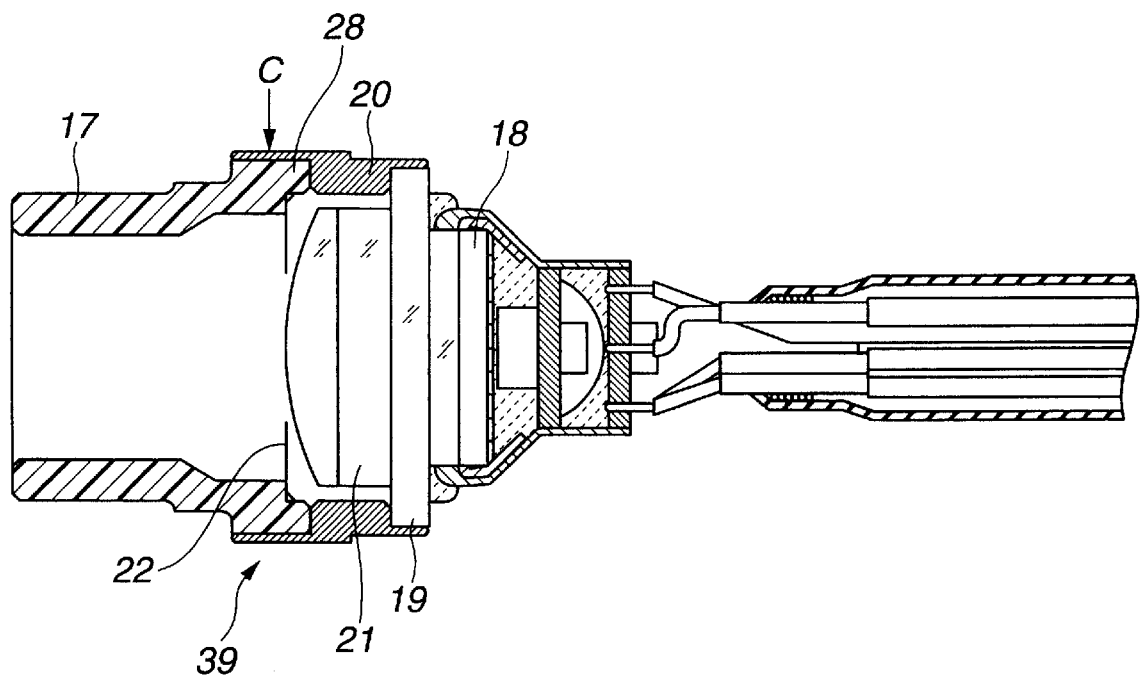

After that, a lens group 21 is positioned in front of the cover glass 19 and joined by translucent adhesive, as shown in FIG. 9. Then, the insulating frame 17 is hermetically joined to the frame 20.

The translucent adhesive resists deterioration, such as peeling, during autoclave sterilization.

The adhesive part is degraded less by steam because it is located within the endoscope and the adhesive is peeled less, as compared to joining the cover glass 13 with the metallic front-end cover frame 14 for example, because the cover glass 19 is adhered to an optical member disposed on the image pickup plane of the solid image pickup device 18, i.e., the optical members are joined, and the difference of coefficients of thermal expansion of the members composing the pasting plane is small.

Figure 10:
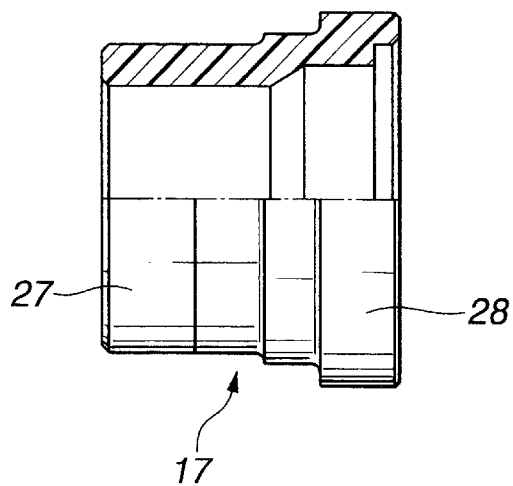

A metal coating surface treatment is disposed on an outer peripheral plane 27, at the front-end side, of the insulating frame 17 mounted on the front-end cover frame 14, and on an outer peripheral plane 28 thereof at the rear-end side mounted on the frame 20, as shown in FIG. 10. No surface treatment by a material having electrical conductivity is disposed between the outer peripheral planes 27 and 28 and on the inner peripheral plane of the insulating frame 17. Therefore, the front-end cover frame 14, which is assembled with the outer peripheral plane 27, is electrically insulated from the frame 20 which is assembled with the outer peripheral plane 28.

The layer formed by the surface treatment of the outer peripheral planes 27 and 28 is composed of a lower nickel layer and an upper metallic layer.

Laser light is irradiated onto the outer peripheral plane of the frame 20 from the direction C after assembling the insulating from 17 with the frame 20, as shown in FIG. 9. Then, gold of the outer peripheral plane 28 of the insulating frame 17 and gold provided at the outermost layer of the inner peripheral plane of the frame 20 melt, respectively, due to the laser. Then, the laser is irradiated all around the frame 20. The frame 20 is cooled thereafter to connect the whole periphery.

It is preferable to use a YAG laser, which may be controlled finely at low output. When a pulse wave laser is irradiated, air-tightness may be assured reliably by superimposing the neighboring pulses by more than 80%.

Although the temperature of the joined part rises to 1000° C. or more during this joining, it does not influence the stop 22 joined within the insulating frame and the adhesive parts because it is local and instantaneous.

Figure 11:
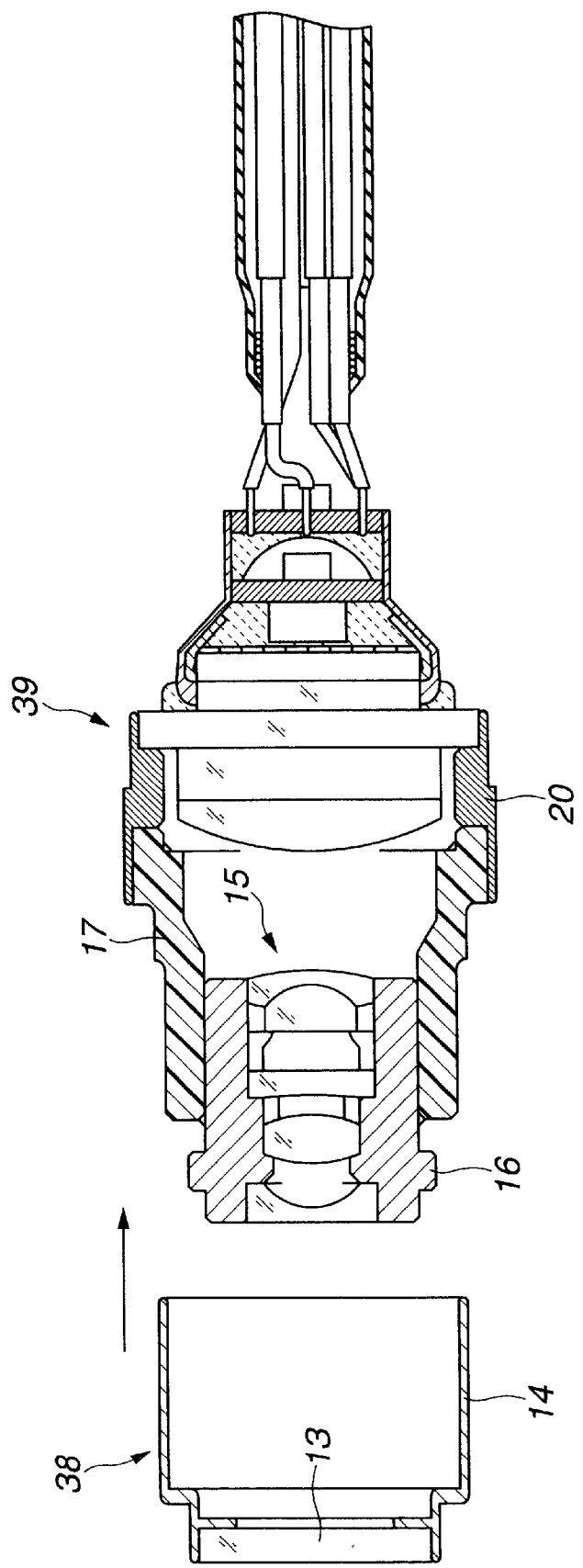

Next, the lens frame 16 in which the objective lens group 15 is assembled is seated in the front-end opening part of the insulating frame 17, as shown in FIG. 11. Then, the position of the lens frame 16 in the direction of optical axis is regulated to control its focus. After that, the lens frame 16 is joined to the insulating frame 17. Here, the lens frame 16 and the objective lens group 15 form an optical unit.

Figure 12:
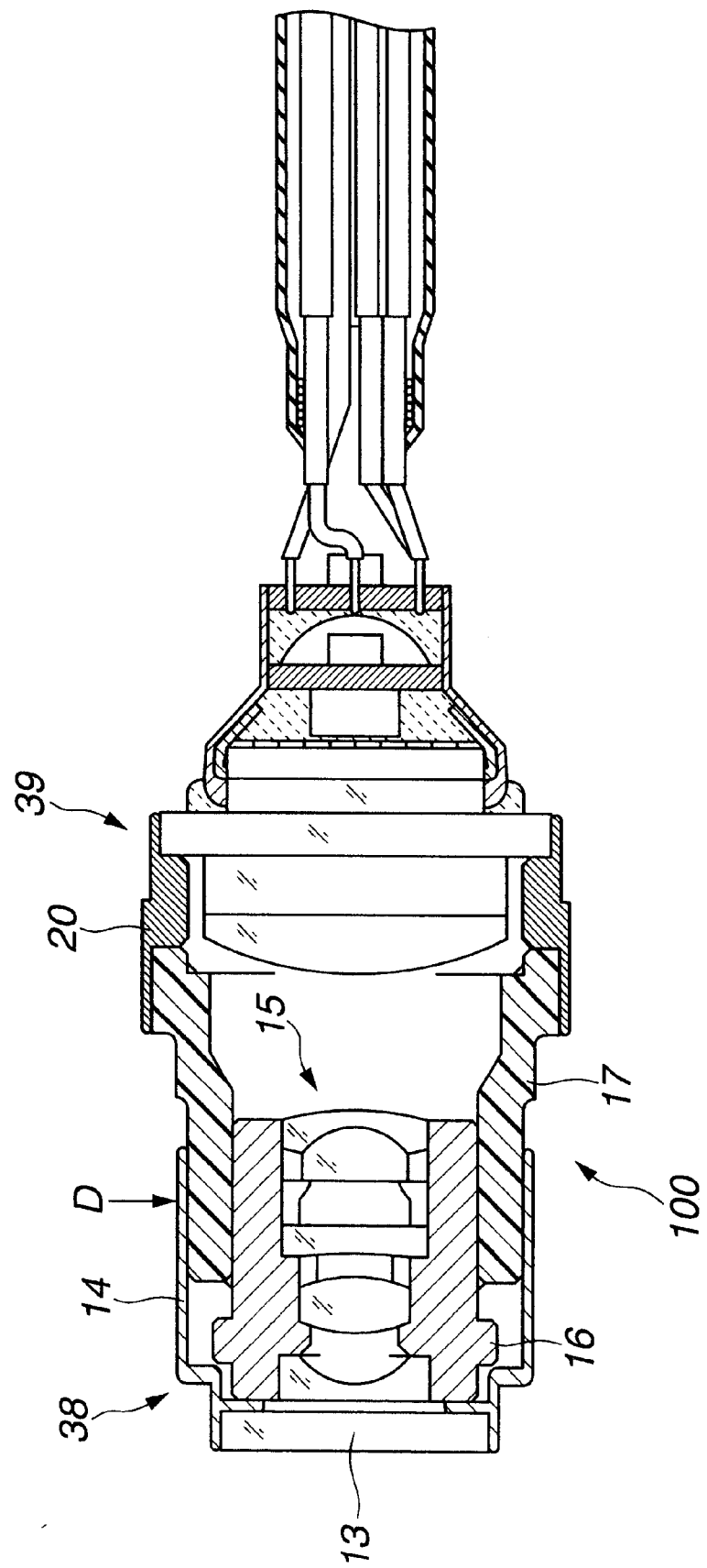

Next, the front-end hermetic optical cover member 38, composed of the cover glass 13 and the front-end cover frame 14, is assembled with the insulating frame 17 so as to cover the objective lens group 15, as shown in FIG. 12. Then, laser is irradiated onto the outer peripheral plane of the front-end cover frame 14 from the direction D. Thus, gold at the outer peripheral plane 27 of the insulating frame 17 and gold at the outermost layer of the inner peripheral plane of the front-end cover frame 14 melt. Then, the laser is irradiated all around the front-end cover frame 14. The front-end cover frame 14 is then cooled to connect the whole periphery.

It is preferable to use a YAG laser which may be controlled finely at low output. When a pulse wave laser is irradiated, air-tightness may be assured reliably by superimposing the neighboring pulses by more than 80%.

Although the temperature of the joined part rises to 1000° C. or more during joining, it does not influence the adhesive part with the lens frame 16 and the objective lens group 15 because it is local and instantaneous.

Thus, the rear-end hermetic optical cover member 39 is hermetically joined with the front-end hermetic optical cover member 38 via the insulating frame 17 and a hermetic objective lens unit 100 including the objective lens group 15 is formed therein.

It becomes possible to reliably prevent the lenses from becoming cloudy by carrying out assembly within an atmosphere of dry inert gas, such as nitrogen gas. It is also possible to reliably prevent the lenses from becoming cloudy by replacing air within the lens unit with the dry inert gas.

The endoscope 1 thus assembled in the predetermined manner is used as a medical tool and is disposed within a chamber of an autoclave sterilizer for sterilization after its use.

The chamber is evacuated in the sterilization pre-step of the autoclave at first.

During the sterilization step, the chamber is filled with high-temperature and high-pressure steam. Thus, high-temperature and high-pressure steam infiltrates the endoscope, thus raising its humidity. Therefore, steam infiltrates he part composed of polymer materials, such as adhesives, even in an endoscope which is constructed to be water-tight as a whole ordinarily. Although the chamber is evacuated during a drying step and the inside of the endoscope is also dried more or less, it is not completely dry.

However, because each joined part of the hermetic objective lens unit 100 is hermetically joined, no steam infiltrates the hermetic objective lens unit 100 even when autoclave sterilization is carried out repeatedly.

Although the high-temperature and high-pressure steam penetrates an O-ring section and adhesive parts, and infiltrates the endoscope during the sterilization step, it is possible to prevent the electrically joined part of the solid image pickup device 18 and the substrate 23 within the front-end section 3 and the electrically joined section of the substrate 23 and the electronic parts and the lead wires of the cables 24 from breaking or deteriorating due to the steam because those regions are sealed by adhesives having low steam permeability and hygroscopic characteristics.

It is also possible to prevent the electrically joined part of the pins 53 within the CCU connector 8 with the lead wires 85 from rusting, breaking or deteriorating due to the steam is sealed by insulating sealant 84 having low steam permeability and hygroscopic characteristics.

The high-temperature and high-pressure steam which has infiltrated the inside of the endoscope tries to affect the angle wire 4a for controlling the waterproof cap 11 of the endoscope during the sterilization step. However, the angle wire 4a is filled with the rust preventive material 57 having the resistance to high-temperature and high-pressure steam in the gap between the respective element wires of the angle wire 4a and the surface of the angle wire 4a is coated by the rust preventive material 57 having the resistance to high-temperature and high-pressure steam as described above. Therefore, the metallic element wires of the angle wire 4a are not directly exposed to the steam. No moisture remains in the gap between the element wires of the angle wire 4a, so that it is possible to prevent the angle wire 4a from rusting. Still more, the surface of the angle coil 4b is also coated by the rust preventive material 57, so that it is possible to prevent the angle coil 4b from rusting and prevent the rust of the angle coil 4b from transferring to the angle wire 4a.

Thus, according to the present embodiment, the provision of the front-end hermetic optical cover member 38 allows the front-end side of the image pickup unit 12, which is exposed to the outside of the endoscope and is severely exposed to the steam of the autoclave, to be covered. Accordingly, the objective lens group 15 will not deteriorate by the high-temperature steam and will not get cloudy by the dew caused by the infiltrated steam, so that autoclave sterilization may be carried out repeatedly.

It is also possible to prevent the steam from infiltrating the objective lens group 15 by sealing the front-end side of the objective lenses, the focus of which must be regulated during the assembly by the front-end hermetic optical cover member 38. Accordingly, it is possible to reduce the diameter of the front-end and to shorten the front-end hard lengthy section of the endoscope even having a bend.

Still more, the provision of the rear-end hermetic optical cover member 39 prevents the steam infiltrating the endoscope from infiltrating the objective lens group 15. Because the air within the hermetic objective lens unit 100 is replaced with the inert gas and almost no steam exists there, no cloud is caused even when the endoscope is cooled quickly.

Because an endoscope is susceptible to autoclave sterilization by the arrangement described above without storing the image pickup device in an air-tight package, it becomes possible to miniaturize and to lower the cost by reducing the size of the insert section 2, for example, as compared to storing the image pickup device within an air-tight package.

The present embodiment allows the adhesives to be used during the focusing, so that the lens frame 16 may be fixed to the insulating frame 17 readily at the focus regulating position.

Still more, because laser, which requires no flux, is used in the final step of covering the hermetically sealing the air-tight optical covering members 38 and 39, it is possible to eliminate a problem that flux enters the hermetic objective lens unit 100 in the final step.

That is, the present embodiment can provide the hermetic objective lens unit 100 which may be assembled in an excellent manner.

Further, the electrical joints, which are liable to be broken by disconnection and the like when external force is applied, is coated by the adhesives and sealant 84, so that the mechanical resistance of the electrical joints to external force is enhanced.

Still more, because the rust preventive material 57 having the resistance to high-temperature and high-pressure steam is filled in the gap between the element wires forming the angle wire 4a and the surface of the angle wire 4a is coated by the rust preventive material 57 having such resistance to high-temperature and high-pressure steam, it is possible to prevent the angle wire 4a from being exposed to the steam and from causing rust.

The same effect may be obtained by partly filling the rust preventive material 57 in the gap between the respective element wires and by coating the rust preventive material 57 on the surface of the angle wire 4a. For instance, it is possible to use the rust preventive material 57 only at regions where rust may be occur.

Thus, the endoscope may be structured so that the bend section experiences no failure even when autoclave sterilization is carried out.

Figure 13:
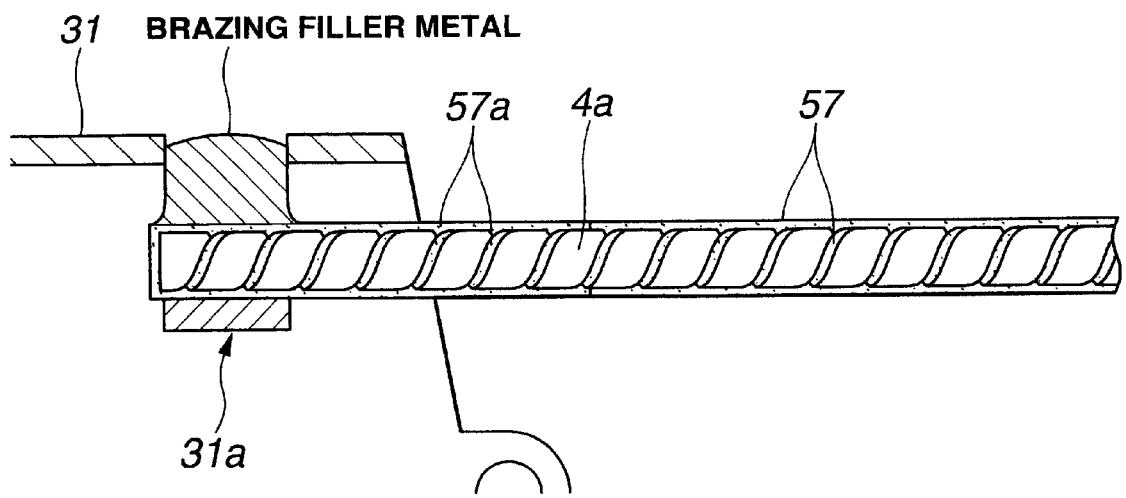

The angle wire 4a may be readily fixed and disposed by filling metallic materials, such as gold, silver and nickel, as a rust preventive material 57a, having resistance to high-temperature and high-pressure steam, in the gap between the respective element wires, at least around the fixing section of the angle wire 4a, by coating the surface of the angle wire 4a with the rust preventive material 57a and by soldering or brazing the angle wire 4a as shown in FIG. 13.

The rust preventive material 57a may be used as a rust preventive coating material and may be used across the whole length of the angle wire 4a. However, when it increases the hardness and cost of the angle wire 4a for example, the rust preventive material 57a is used only around an angle wire fixing part 31a and the rust preventive material 57 explained in FIG. 4 for example is used in the regions other than that part.

The rust preventive coating using the rust preventive material 57a such as gold, silver and nickel is effective in using the angle wire 4a which is made of a material, e.g., tungsten wire, which cannot be brazed or soldered.

It become also possible to fix the angle wire 4a by soldering or brazing without using flux by using gold, silver, nickel or the like having good wettability as the rust preventive material 57a and by using the rust preventive material 57a having good wettability to the region where the angle wire 4a is to be fixed. Thereby, the part around the fixing section will not rust due to flux.

The hermetic joining has been carried out by melting gold with a laser in the embodiment described above. The hermetic jointing may be carried out by welding other metals and by molten glass. The metal welding includes fusion welding typified by laser welding and electron beam welding, pressure welding, typified by resistance welding, braze welding, such as brazing and soldering. Hermetic joining may be carried out by these.

Further, even if adhesive is used, airtightness may be assured by the front-end hermetic optical cover member 38 if the front-end cover frame 14 is joined with the cover glass 13 more air-tightly than the lens frame 16 joined with the insulating frame 17 and the lens frame 16 joined with the lens at the front-end of the objective lens group 15.

Further, although the cover glass 19, positioned at the basal end side from the objective lens group 15, has been hermetically joined with the frame 20 and the frame 20 with the insulating frame 17, respectively, in the present embodiment, their joints are less attacked by steam during autoclave sterilization because they are positioned within the endoscope. Therefore, even if adhesive is used, steam barely infiltrates the objective lens group 15 and no failure of view field occurs due to the front-end hermetic optical cover member 38.

Although the explanation has been made regarding a medical endoscope which is sterilized by the autoclave in the present embodiment, the endoscope is not limited to a medical endoscope and the invention may be applied to any endoscope which is to be sterilized by steam, an endoscope which contacts medicinal solutions and an industrial endoscope which is used under high-humidity environments, for example.

The embodiment regarding the objective lens unit described above may be also applied to various lens systems of an endoscope unit, e.g., an eyepiece lens of a fiber scope and an optical system of a camera head attached to an eyepiece section. The lens unit adopting this configuration can block the infiltration of steam and can be compact. It may be applied also to a hard scope utilizing a relay lens as an image pickup means as a matter of course.

A second embodiment of the invention will be explained below with reference to FIGS. 14 and 15.

Figure 14:
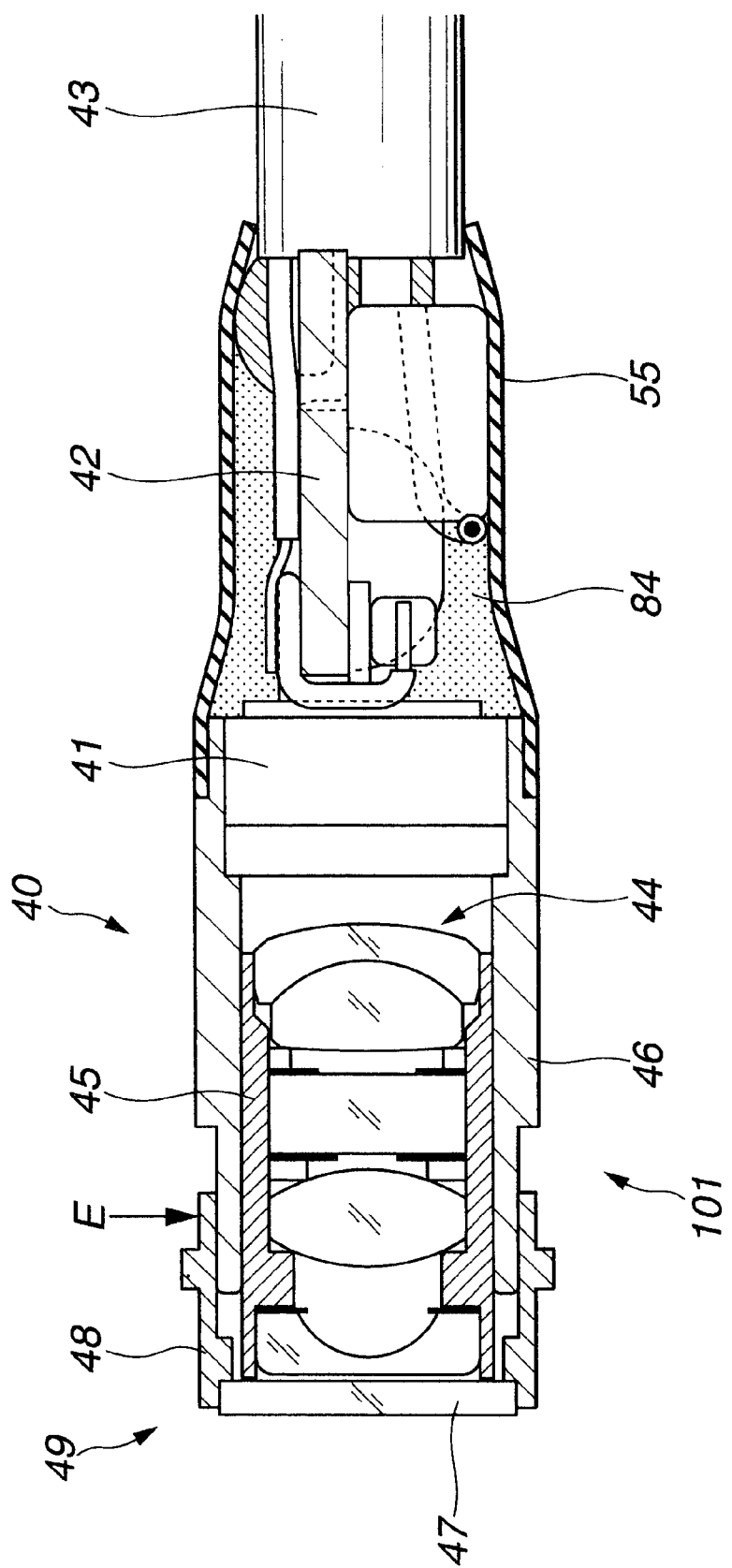

FIG. 14 shows a structural example of a image pickup unit 40 having no insulating frame.

The image pickup unit 40 comprises a solid image pickup device 41, a substrate 42 on which electronic parts are mounted, a cable 43 electrically connected to the solid image pickup device 41 via the substrate 42, an objective lens group 44 disposed in front of the solid image pickup device 41, a lens frame 45 to which the objective lens group 44 is assembled, a lens frame supporting frame 46, which is a metallic optical unit supporting frame for holding the lens frame 45 by positioning in the direction of optical axis, a sapphire cover glass 47 disposed in front of the objective lens group 44, and a metallic front-end cover frame 48 hermetically joining the cover glass 47.

Figure 15:
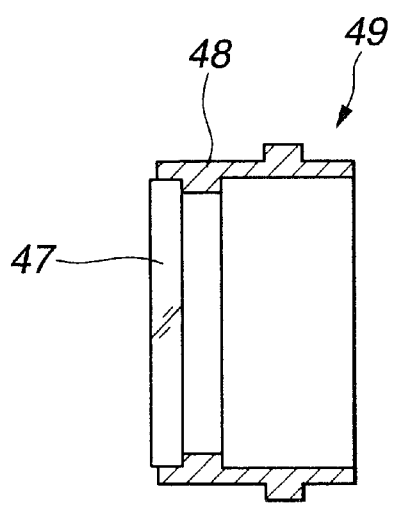

The cover glass 47 is hermetically joined with the metallic front-end cover frame 48 by means of brazing or soldering, thus composing a front-end hermetic optical covering member 49 as shown in FIG. 15. A metal coating surface treatment as shown in the first embodiment is implemented on the outer peripheral plane of the cover glass 47 to metallize the outermost layer. Then, when flux is used during brazing or soldering, the flux is fully cleaned and removed when the front-end hermetic optical covering member 49 is constructed.

Plating such as gold plating, nickel plating or tin plating is implemented on the front-end cover frame 48 to facilitate the brazing or soldering.

The cover glass 47 may be hermetically joined with the front-end cover frame 48 by laser or by molten glass similarly to the first embodiment after the brazing and soldering.

The sheath of the solid image pickup device 41 is hermetically joined with the lens frame supporting frame 46 by soldering, brazing, welding, molten glass or the like in the present embodiment. When the sheath of the solid image pickup device 41 is non-metal, the metal coating surface treatment may be carried out similarly to the outer peripheral plane of the cover glass 47.

Fluoro-rubber sealant having low steam permeability or the sealant 84 is filled around the solid image pickup device 41 and the substrate 42 and a thermal shrinkage tube 55 made of fluoro-resin, for example, having low steam permeability is coated further around that. This arrangement prevents the solid image pickup device 41 and the substrate 42 from being exposed to steam during autoclave sterilization.

Next, the procedure for assembling the endoscope according to the present embodiment will be explained.

At first, the sheath of the solid image pickup device 41 is hermetically joined to the lens frame supporting frame 46. Then, the position of the lens frame 45 to which the objective lens group 44 is assembled beforehand is adjusted in the direction of the optical axis within the lens frame supporting frame 46 to regulate the focus. Then, when the lens frame 45 is focused, it is adhered and fixed to the lens frame supporting frame 46.

Next, the front-end hermetic optical covering member 49 composed of the glass 47 and the front-end cover frame 48 is covered so as to cover the front-end side of the objective lens group 44. Then, the opening side of the front-end cover frame 48 is hermetically joined to the lens frame supporting frame 46.

Laser welding is suitable as the hermetic joining method because both members of the front-end cover frame 48 and the lens frame supporting frame 46 are metal. The solid image pickup device 41 and other parts already assembled will not be destroyed because heating is only local during laser welding. Laser welding also has a benefit in that the hermetic joining may be carried out without using flux in the final step of hermetically closing the front-end cover frame 48.

Laser light is irradiated around the whole periphery from the direction of arrow E in carrying out laser welding. Thereby, a hermetic objective lens unit 101 in which the objective lens group 44 is hermetically concealed is created.

Thus, according to the present embodiment, no steam infiltrates the hermetic objective lens unit 101 in which the objective lens group 44 is stored even when the endoscope using the image pickup unit 40 is repeatedly sterilized in the autoclave similarly to the first embodiment.

The present embodiment also allows the hermetic objective lens unit 101 storing the objective lens group 44, which is smaller than that of the first embodiment, to be created.

Although the solid image pickup device 41 has been hermetically joined with the lens frame supporting frame 46 positioned at the basal end side from the objective lens group 44 in the present embodiment, the joint is less attacked by the steam of the autoclave because it is located within the endoscope. Therefore, the steam barely infiltrates the objective lens group 44 and no failure of the view field occurs due to the front-end hermetic optical covering member 49 when they are concealed to a certain level by adhesives or the like instead of hermetically joining by brazing or welding.

Still more, although the front-end cover frame 48 has been hermetically joined with the lens frame supporting frame 46 by the laser welding in the present embodiment, the adhesive will not peel off and the steam barely infiltrates the objective lens group 44 due to the front-end hermetic optical covering member 49 when they are concealed by adhesive or the like to a certain level for three reasons: 1) this joint is located within the endoscope, 2) the front-end cover frame 48 and the lens frame supporting frame 46 are both metallic parts having a coefficient of thermal expansion preferably are almost equal, and 3) the length of engagement of this joint may be longer than the engaging section of the cover glass 47 and the front-end cover frame 48.

Because the joint of the cover glass 47 and the front-end cover frame 48 composing the front-end hermetic optical covering member 49 is directly influenced by the steam of the autoclave sterilization and is the part where the optical member is joined with metal, it is preferable to reliably and hermetically join by brazing, soldering or the like.

Figure 16:
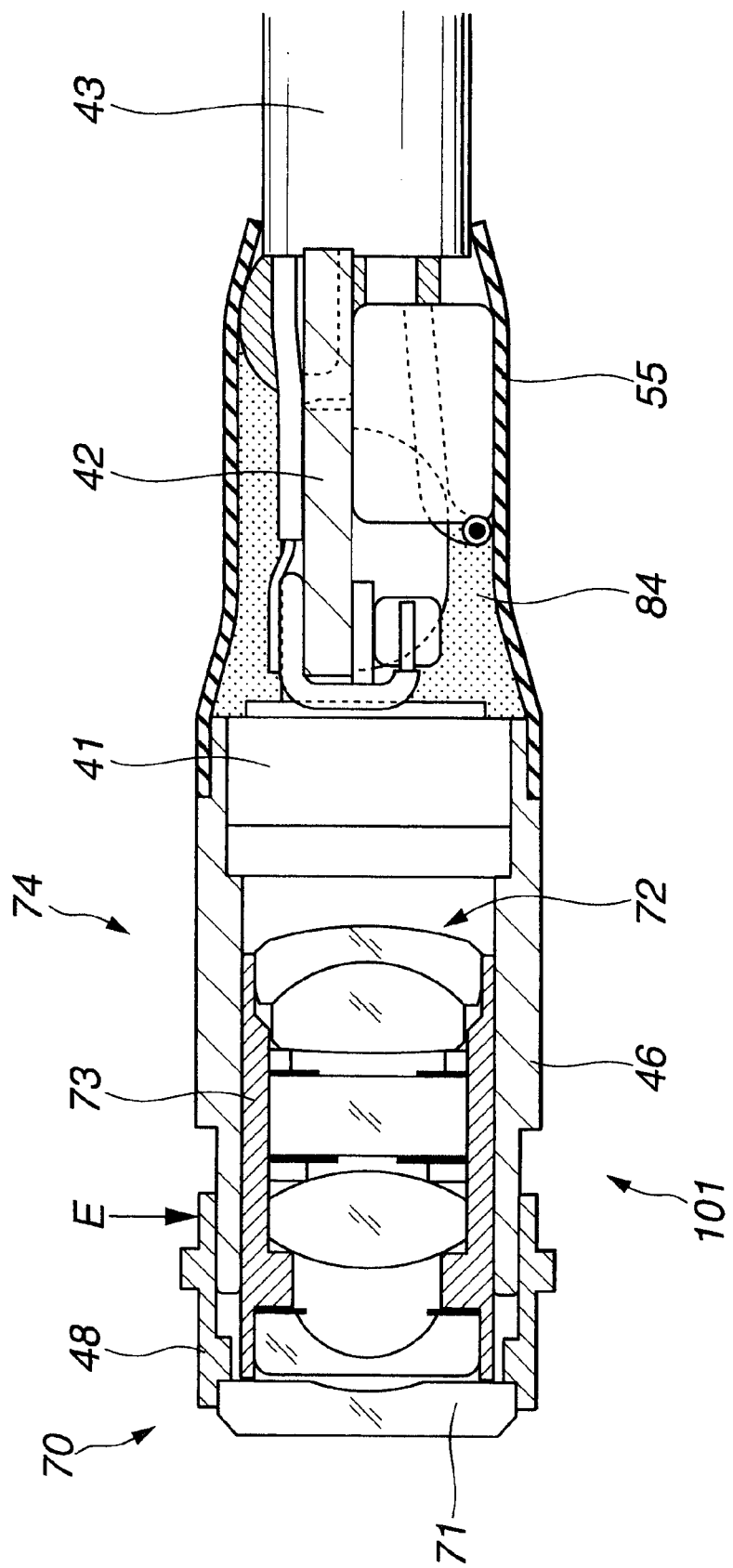

A third embodiment of the invention will be explained below with reference to FIGS. 16 through 18.

According to the present embodiment, an optical window of a front-end hermetic optical covering member 70 is formed of a concave lens 71 which is made of sapphire or a high-heat resistant and high-steam resistant optical member. The structure other than that is similar to the second embodiment. The same members are denoted by the same reference numerals and an explanation thereof will be omitted here.

According to the assembly method of the endoscope of the present embodiment, a lens frame 73, in which the objective lens group 72, except the concave lens 71, which is the optical window, is assembled, is moved in the direction of the optical axis within the lens frame supporting frame 46 to control the focus. Then, the lens frame 73 is adhered and fixed to the lens frame supporting frame 46 at the position where the objective lens group 72 is in focus. The above-mentioned focus control work may be carried out because the objective lens group 72 is an optical system which can form an image on the solid image pickup device 41 even without the concave lens 71.

Figure 18:
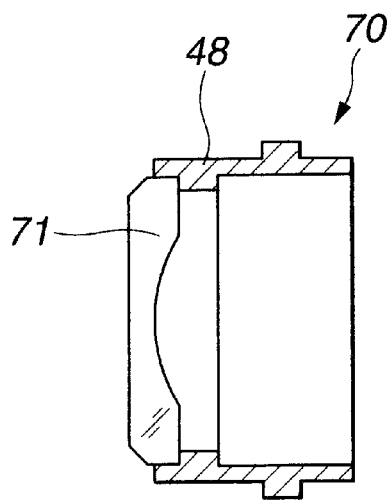
Figure 17:
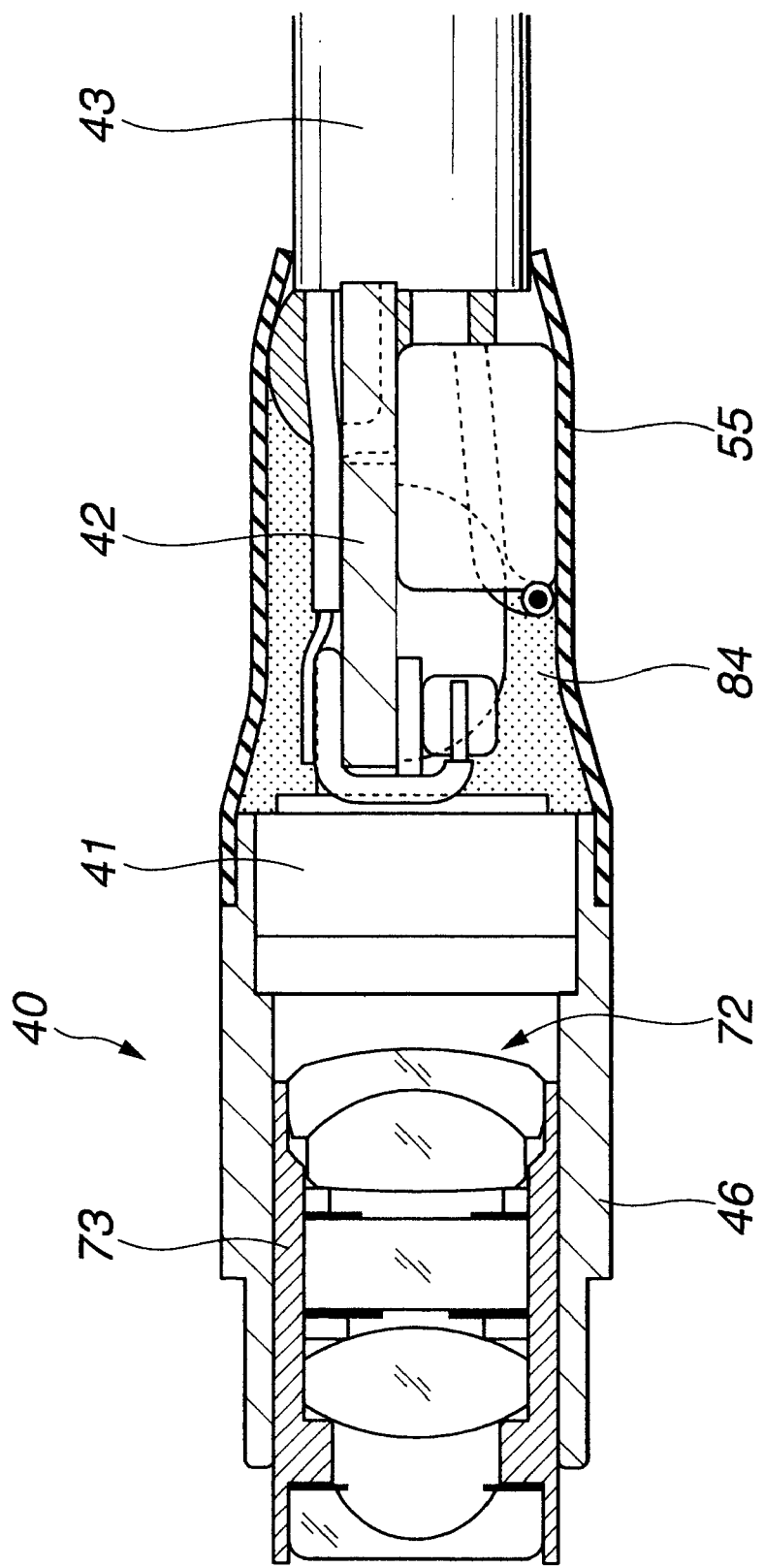

After controlling the focus, the front-end hermetic optical covering member 70 composed of the concave lens 71 and the front-end cover frame 48 as shown in FIG. 18 is covered so as to coat the front-end side of the objective lens group 72 as shown in FIG. 17 and the opening of the front-end cover frame 48 is hermetically joined with the lens frame supporting frame 46.

Thereby, an optical system, which is wider than the optical system of the objective lens group 72 from which the concave lens 71 is removed, may be attained when the focus is adjusted. The optical system combining the concave lens 71 and the objective lens group 72 can also form an image on the solid image pickup device 41.

Thus, the present embodiment can provide an image pickup unit 74 having an angle of view field that is wider than that of the second embodiment. This image pickup unit is small and can be assembled favorably similarly to that of the second embodiment.

Figure 19:
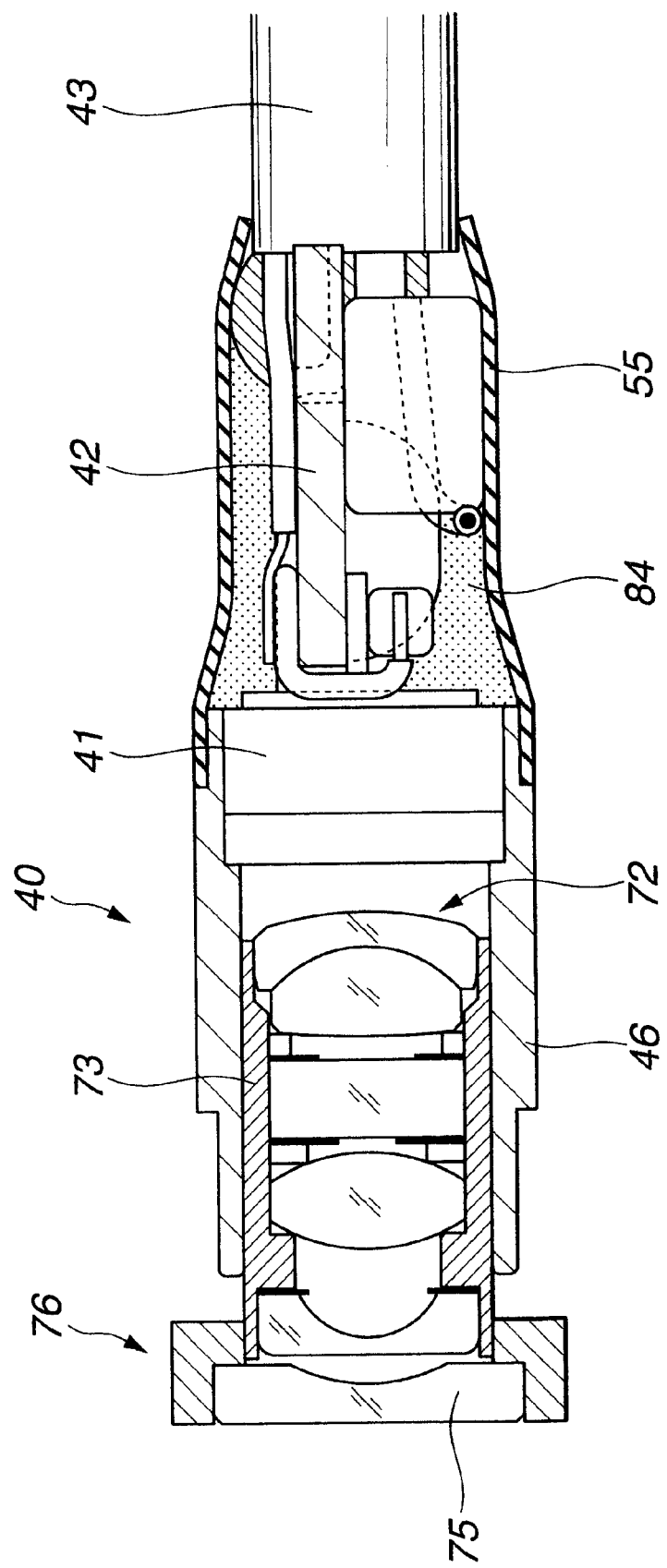

When the objective lens group 72 from which the concave lens 71 is removed is an optical system which is unable to form an image completely, the focus is adjusted by using a lens set 76 in which a dummy concave lens 75 is assembled as shown in FIG. 19. Then, after adjusting the focus, the lens set 76 is removed and the front-end hermetic optical covering member 70 is assembled again as shown in FIG. 17. This assembly method is effective when the optical system in which the objective lens group 72 excluding the concave lens 71 is unable to form an image completely.

Figure 20:
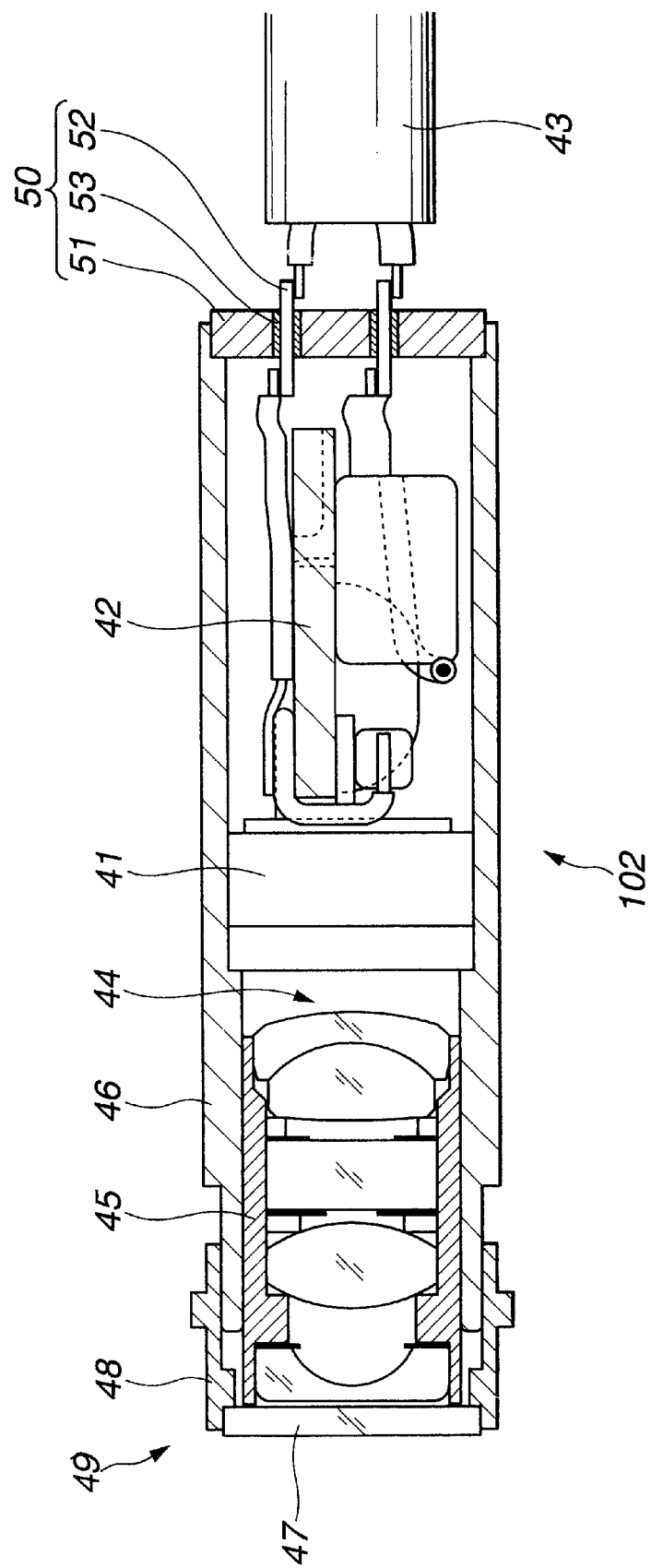
FIG. 20 is a section view of a hermetic objective lens unit according to a fourth embodiment of the invention.

A fourth embodiment of the invention will be explained below with reference to FIG. 20.

As shown in the figure, the solid image pickup device 41 is not hermetically joined with the lens frame supporting frame 46 and is fixed while being inserted into the lens frame supporting 46 in the present embodiment. The lens frame supporting frame 46 also extends to the basal end side and covers the outer periphery of the solid image pickup device 41 and the substrate 42. Further, a hermetic connector 50 is hermetically at the opening of the basal end side of the lens frame supporting frame 46.

The hermetic connector 50 comprises a metallic hermetic connector main body 51, contact pins 52 for electrically connecting the front-end side and the basal end side of the hermetic connector and insulating concealing sections 53 for insulating the contact pins 52 from the hermetic connector main body 51 and for hermetically holding them. The front-end side and the basal end side of the hermetic connector 50 is hermetically parted by hermetically joining the hermetic connector 50 with the opening at the basal end side of the lens frame supporting frame 46. The solid image pickup device 41, the substrate 42 and the cable 43 are electrically connected by the contact pins 52. The insulating concealing section 53 is made of glass or the like. The structure of the front-end side otherwise is the same as that of the second embodiment and the same members are denoted by the same reference numerals. An explanation thereof will be omitted here.

Thus, a hermetic objective lens unit 102 in which not only the objective lens group 44 but also the solid image pickup device 41 and the substrate 42 on which the electronic parts are mounted are also hermetically concealed is formed by the front-end hermetic optical covering member 49, the lens frame supporting frame 46 and the hermetic connector 50.

This arrangement allows the solid image pickup device 41, the substrate 42 and the electronic parts mounted on the substrate 42 to be protected from the steam of the autoclave at a level higher than that of the second embodiment. As a result, no steam infiltrates the hermetic objective lens unit 102 storing the objective lens group 44, the solid image pickup device 41 and the substrate 42 even when the endoscope using the image pickup unit of the present embodiment is repeatedly sterilized in the autoclave similarly to the first embodiment.

Thus, the present embodiment allows the solid image pickup device 41 and the electronic parts on the substrate 42 to be protected from the steam of the autoclave at a level higher than that of the first and the second embodiment in addition to the effects of the first and second embodiments. It prolongs the life of these devices and parts and prevents the wires on the substrate 42 from rusting, thus obtaining high reliability.

The lens frame supporting frame 46 may be divided into two parts or more around the part where the solid image pickup device 41 is fixed for example by considering the assembly thereof. Each joint of the lens frame supporting frame 46 thus divided into a plurality of parts is hermetically joined by laser welding, soldering or the like in such a case.

Figure 21:
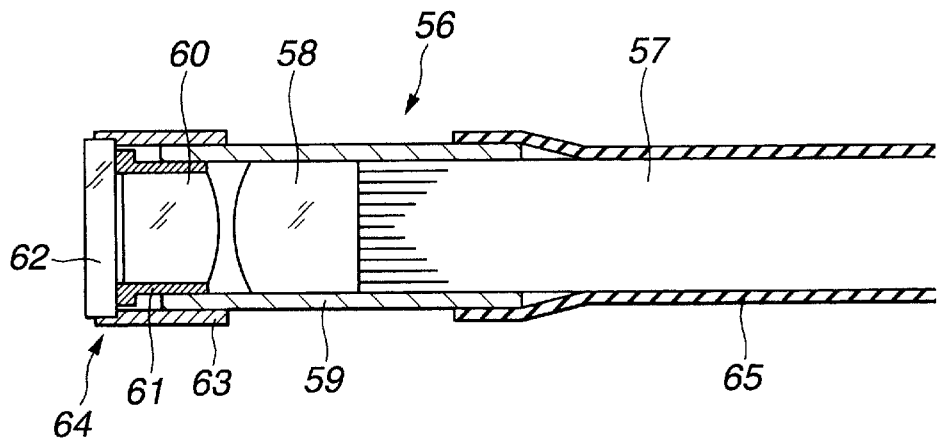
FIG. 21 is a section view of an image pickup unit according to a fifth embodiment of the invention.

A fifth embodiment of the invention will be explained below with reference to FIG. 21.

According to the present embodiment, an image guide fiber 57 is used instead of the solid image pickup device and the cable as an image pickup means of an image pickup unit 56, i.e., as image input means and image transmitting means, as shown in the figure.

A first objective lens 58 is fixed to the front-end of the image guide fiber 57 by translucent adhesive. A fiber frame 59, which is an optical unit supporting frame, is hermetically joined by molten glass or the like to the outer periphery of the front-end portion of the image guide fiber 57. Then, the front-end portion of a sheath tube 65, made of fluoro-resin for example, having low steam permeability and coating the image guide fiber 57 is joined at the read end of the fiber frame 59.

A lens frame 61 is engaged and inserted into the front-end side inner hold of the fiber frame 59. A second objective lens 60 is assembled to the lens frame 61. The position of this lens frame 61 is adjusted in the direction of the optical axis and is adhered and fixed to the fiber frame 59 at the position where the second objective lens 60 is in focus.

A front-end hermetic optical covering member 64, composed of a cover glass 62 and a front-end cover frame 63, which is hermetically joined to the cover glass 62, is hermetically joined around the front-end portion of the fiber frame 59 so as to cover in front of the second objective lens 60.

Various joining methods explained in the first through fourth embodiments may be adopted as the hermetic joining method.

No steam infiltrates the first and second objective lenses 58 and 60 even when the endoscope using the image pickup unit is repeatedly sterilized by the autoclave similarly to the embodiments described above.

Thus, the effects that no steam infiltrates, the objective lenses 58 and 60 do not get cloudy and do not deteriorate may be obtained by the fiber scope using the image guide fiber 57 even when it is repeatedly sterilized by the autoclave similarly to the first and second embodiments. Almost no steam infiltrates the objective lenses 58 and 60 and no failure of the view field occurs even when adhesive is used because the joint of the outer periphery of the image guide fiber 57 and the fiber frame 59 is located within the endoscope.

Figure 22:
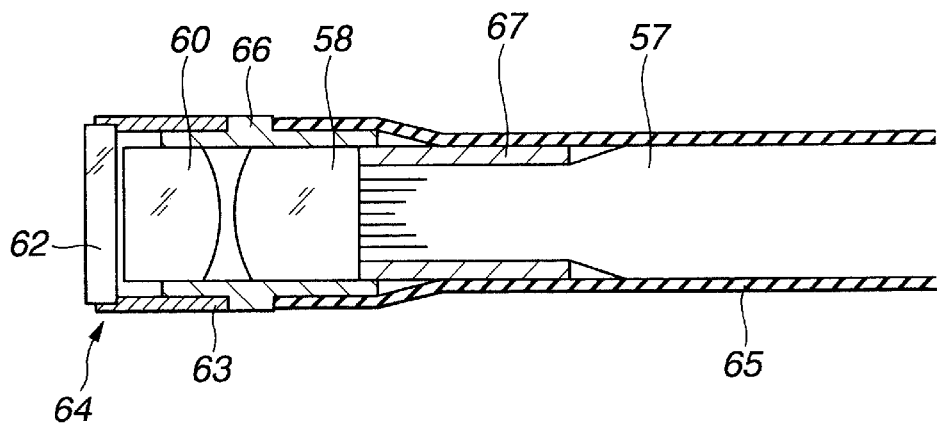
FIG. 22 is a section view of an image pickup unit according to a sixth embodiment of the invention.

A sixth embodiment of the invention will be explained with reference to FIG. 22.

As shown in the figure, the first objective lens 58 is fixed to the front-end of the image guide fiber 57 inserted into a fiber mouthpiece 67 with no air layer by translucent adhesive in the present embodiment. A lens frame 66, which is an optical unit supporting frame, is hermetically joined to the outer periphery of the first objective lens 58.

The second objective lens 60 composing the optical unit is directly inserted and disposed in the inner hole at the front-end side of the lens frame 66. Then, the position of the second objective lens 60 is adjusted in the direction of the optical axis with respect to the lens frame 66 and is adhered and fixed to the lens frame 66 at the position where the second objective lens 60 is in focus.

A front-end cover frame 63 of the front-end hermetic optical covering member 64 abuts a projection of the lens frame 66 and is hermetically joined by laser in this state. At this time, the cover glass 62 faces the second objective lens 60 while leaving a predetermined gap without any contact.

No steam infiltrates the front-end surface of the second and first objective lenses 60 and 58 even when the endoscope using the image pickup unit is repeatedly sterilized by the autoclave similarly to the first embodiment.

Further, because the rear-end plane of the first objective lens 58 is fixed to the front-end of the image guide fiber 57 with no air layer by the translucent adhesive, this plane will not get cloudy due to the steam.

Thus, the present embodiment allows the lens frame 61 of the fifth embodiment to be eliminated in addition to the effect of the fifth embodiment. It also becomes unnecessary to hermetically join the outer periphery of the image guide fiber 57 with the lens frame 66.

Figure 23:
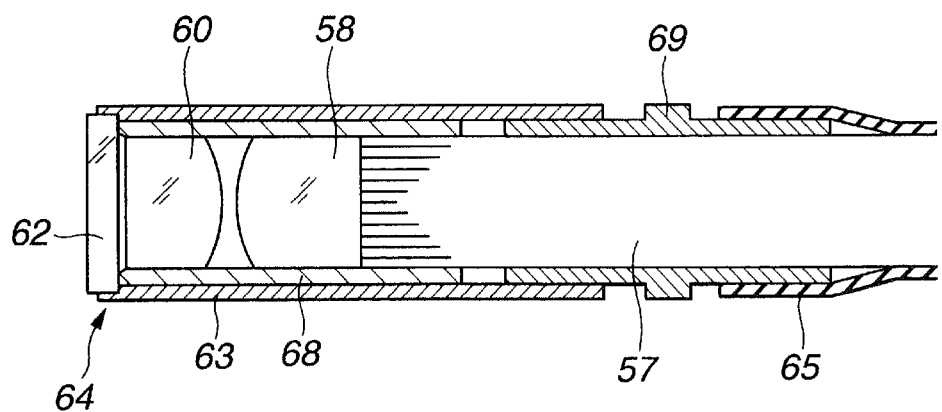
FIG. 23 is a section view of an image pickup unit according to a seventh embodiment of the invention.

A seventh embodiment of the invention will be explained with reference to FIG. 23.

As shown in the figure, the second objective lens 60 is fixed around the front-end portion within a lens frame 68 in the present embodiment. Then, the image guide fiber 57 to which the first objective lens 58 is fixed by the translucent adhesive by the front-end thereof is inserted into the rear-end side of the lens frame 68.

The position of the image guide fiber 57 first objective lens 58 is adjusted in the direction of the optical axis with respect to the lens frame 68 and is joined and fixed by adhesive or the like at the position where the first objective lens 58 is in focus.

The part around the front-end portion of the image guide fiber 57 is formed to be hard. Then, a fiber frame 69 is hermetically fixed to a part of the outer periphery. The front-end hermetic optical covering member 64 composed of the cover glass 62 and the front-end cover frame 63 is hermetically joined around the front-end portion of the fiber frame 69.

Accordingly, the position of the fiber frame 69 of the present embodiment may be adjusted relatively by moving in the direction of the optical axis with respect to the second objective lens 60 and the lens frame 68.

In this case, the optical unit is composed of the second objective lens 60 and the lens frame 68 and the fiber frame 69 functions as an optical unit supporting frame through the hard section of the image guide fiber 57. The present embodiment thus allows the same effects as that of the fifth embodiment to be obtained.

It is apparent that the different embodiments may be structured based on the present invention without departing from the spirit and scope of the invention. Therefore, the invention is not limited by its specific embodiment and is limited only by the appended claims.

What is claimed is:

1. An endoscope comprising:
    a light transmitting member for transmitting incident light;
    a frame having an inner wall and an outer wall, said light transmitting member being fixed to said inner wall of said frame; and
    a cover hermetically joined to said outer wall of said frame to cover said light transmitting member, said cover having an optical window for guiding light to said light transmitting member.

2. The endoscope according to claim 1, wherein said light transmitting member comprises an optical unit including at least one optical lens.

3. The endoscope according to claim 2, wherein the frame defines a hermetically sealed inner space.

4. The endoscope according to claim 2, wherein said cover comprises:
    an optical member which forms said optical window; and
    an edge portion defining an opening for holding said optical member, said optical member being hermetically joined to said edge portion.

5. The endoscope according to claim 2,
    wherein said frame having said optical unit fixed thereto is a first frame, said optical unit comprises a second frame having an inner wall and an outer wall, said outer wall of said second frame being fixed to said inner wall of said first frame, and said at least one optical lens being fixed to said inner wall of said second frame.

6. The endoscope according to claim 2, wherein said optical unit is a single lens which is fixed to said second frame.

7. The endoscope according to claim 2, wherein said cover is joined to said outer wall of said frame by welding, soldering, brazing or molten glass.

8. The endoscope according to claim 2, wherein said optical window is a sapphire glass, a cover glass or a lens.

9. The endoscope according to claim 1, wherein said light transmitting member comprises an image guide fiber, said cover being provided in front of a front end of said image guide fiber.

10. The endoscope according to claim 9, wherein said optical window is a cover glass.

11. The endoscope according to claim 9, wherein an optical lens is fixed to said front end of said image guide fiber.

12. The endoscope according to claim 1, further comprising:
an image pickup device in an inner space formed by said inner wall of said frame;
a substrate in said inner space, said substrate being electrically connected to said image pickup device,
a hermetic body for hermetically closing said inner space of said frame, said hermetic body being hermetically joined to said frame, and said hermetic body being provided with through holes,
conductive members extending through said through holes into said inner space, said conductive members being electrically connected to said substrate; and
sealing members for hermetically sealing said conductive members in said through holes.

13. A method of assembling an endoscope, the method comprising:
providing a frame having an inner wall and an outer wall;
fixing a light transmitting member to said inner wall of said frame;
fitting a cover having an optical window for guiding light to said light transmitting member to said outer wall of said frame; and hermetically joining said cover to said outer wall of said frame.

14. An endoscope comprising:
a hollow first frame, said first frame having an inner wall and an outer wall;
a first optical member arranged in a first inner space defined by said first frame;
a hollow second frame, said second frame having an inner wall and an outer wall, and said first frame being received in a second inner space defined by said second frame;
a third frame hermetically joined to said outer wall of said second frame; and
a second optical member provided in said third frame, said second optical member guiding light to said first optical member.

15. The endoscope according to claim 14, wherein said third frame comprises:
an edge portion defining an opening for holding said second optical member, said second optical member being hermetically joined to said edge portion.

16. The endoscope according to claim 15, wherein a hermetically sealed third inner space is defined by the hermetically joining of said second frame and said third frame to each other, and by the joining of said edge portion of said third frame and said second optical member to each other.

17. The endoscope according to claim 14, wherein said outer wall of said second frame is joined to said third frame by welding, soldering, brazing or molten glass.

18. The endoscope according to claim 14, wherein said second optical member is a sapphire glass, a cover glass, and a lens.

19. The endoscope according to claim 14, further comprising:
an image pickup device provided in an inner space formed by said inner wall of said second frame;
a substrate in said inner space, said substrate being electrically connected to said image pickup device,
a hermetic body for hermetically closing said inner space of said second frame, said hermetic body being hermetically joined to said second frame, and said hermetic body being provided with through holes;
conductive members extending through said through holes into said inner space, said conductive members being electrically connected to said substrate; and
sealing members for hermetically sealing said conductive members in said through holes.

20. An endoscope comprising:
an image guide fiber for transmitting an optical image;
a frame having an inner wall and an outer wall, said frame covering an outer surface of said image guide fiber;
an optical unit having at least one optical lens, said optical unit being optically coupled to said image guide fiber; and
a cover hermetically joined to said outer wall of said frame to cover said optical unit, said cover having an optical window for guiding light to said at least one optical lens.

21. The endoscope according to claim 20, wherein said inner wall of said frame is hermetically joined to an outer surface of said image guide fiber.

22. The endoscope according to claim 20, wherein said cover comprises:
an optical member which forms said optical window; and
an edge portion defining an opening for holding said optical member, said optical member being hermetically joined to said edge portion.

23. The endoscope according to claim 20, wherein said cover is joined to said outer wall of said frame by welding, soldering, brazing or molten glass.

24. The endoscope according to claim 20, wherein said optical window is a sapphire glass, a cover glass or a lens.

25. An endoscope comprising:
an optical unit having at least one optical lens;
fixing means for fixing said optical unit, said fixing means having an inner wall and an outer wall, said optical unit being fixed to said inner wall of said fixing means;
cover means hermetically joined to said outer wall of said fixing means to cover said optical unit, said cover means having an optical window for guiding light to said at least one optical lens.

26. The endoscope according to claim 25, wherein said cover means is joined to said outer wall of said fixing means by welding, soldering, brazing or molten glass.

27. The endoscope according to claim 25, wherein said optical window is a sapphire glass, a cover glass or a lens.

28. The endoscope according to claim 25, further comprising:

- an image pickup device provided in an inner space formed by said inner wall of said fixing means;
- a substrate in said inner space, said substrate being electrically connected to said image pickup device;
- a hermetic body for hermetically closing said inner space of said fixing means, said hermetic body being hermetically joined to said fixing means, and said hermetic body being provided with through holes;
- conductive members extending through said through holes into said inner space, said conductive members being electrically connected to said substrate; and
- sealing members for hermetically sealing said conductive members in said through holes.

* * * * *